US006207874B1

(12) United States Patent
Felton et al.

(10) Patent No.: US 6,207,874 B1
(45) Date of Patent: Mar. 27, 2001

(54) CUSTOMIZED AESTHETIC AND RECONSTRUCTIVE TEMPORARY TATTOO AND METHOD FOR MAKING SAME

(76) Inventors: Jennifer L. Felton, 6586 90th Ave., Storm Lake, IA (US) 50588; R. Coleen Stice, 6510 Sorensen Pkwy., Suite 102, Omaha, NE (US) 68152

( * ) Notice: Subject to any disclaimer, the term of this patent is extended or adjusted under 35 U.S.C. 154(b) by 0 days.

(21) Appl. No.: 09/426,138

(22) Filed: Oct. 22, 1999

(51) Int. Cl.[7] ............................. A61F 13/00; B41M 3/12
(52) U.S. Cl. ........................ 602/42; 602/52; 602/54; 428/914
(58) Field of Search ........................ 428/195, 201, 428/202, 203, 343, 352, 914; 602/41–59

(56) References Cited

U.S. PATENT DOCUMENTS

| | | | |
|---|---|---|---|
| 2,851,805 | 9/1958 | Allen | 41/10 |
| 4,594,276 | 6/1986 | Relyea | 428/40 |
| 4,735,754 | 4/1988 | Buckner | 462/40.1 |
| 4,778,465 | 10/1988 | Wilkins | 623/8 |
| 5,052,418 | 10/1991 | Miller | 132/319 |
| 5,421,765 | 6/1995 | Lehmann et al. | 446/296 |
| 5,470,351 | 11/1995 | Ross et al. | 607/95 |
| 5,569,237 | 10/1996 | Beckenstein | 606/1 |
| 5,578,353 | 11/1996 | Drew, III | 428/43 |
| 5,727,567 | 3/1998 | Carnaby et al. | 128/857 |
| 5,741,290 | 4/1998 | Hsieh | 606/186 |
| 5,798,062 | 8/1998 | Thielbar | 264/40.1 |
| 5,816,269 | 10/1998 | Mohammed | 132/319 |
| 5,817,143 | 10/1998 | Perry | 607/88 |
| 5,817,385 | 10/1998 | Stanislav | 428/40.2 |
| 5,836,998 | 11/1998 | Mueller et al. | 607/95 |

Primary Examiner—Kim M. Lewis
(74) Attorney, Agent, or Firm—Zarley, McKee, Thomte, Voorhees & Sease

(57) ABSTRACT

The present invention relates to a temporary tattoo used for aesthetic and reconstructive purposes to match one member of a paired body part that has been lost or to cover a portion of the body that is aesthetic unappealing or undesirable. The present invention also includes the method of making a customized temporary tattoo used for either reconstructive or aesthetic purposes such as scar coverage.

8 Claims, 2 Drawing Sheets

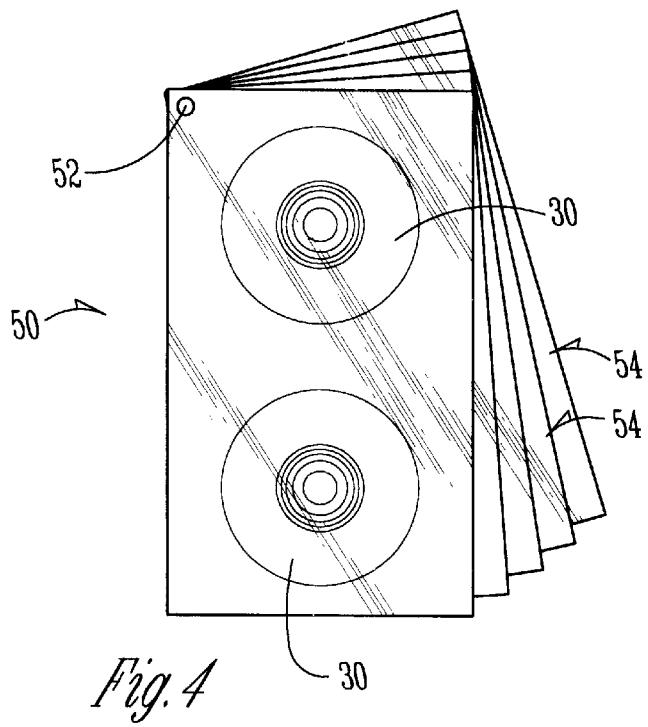
Fig. 4
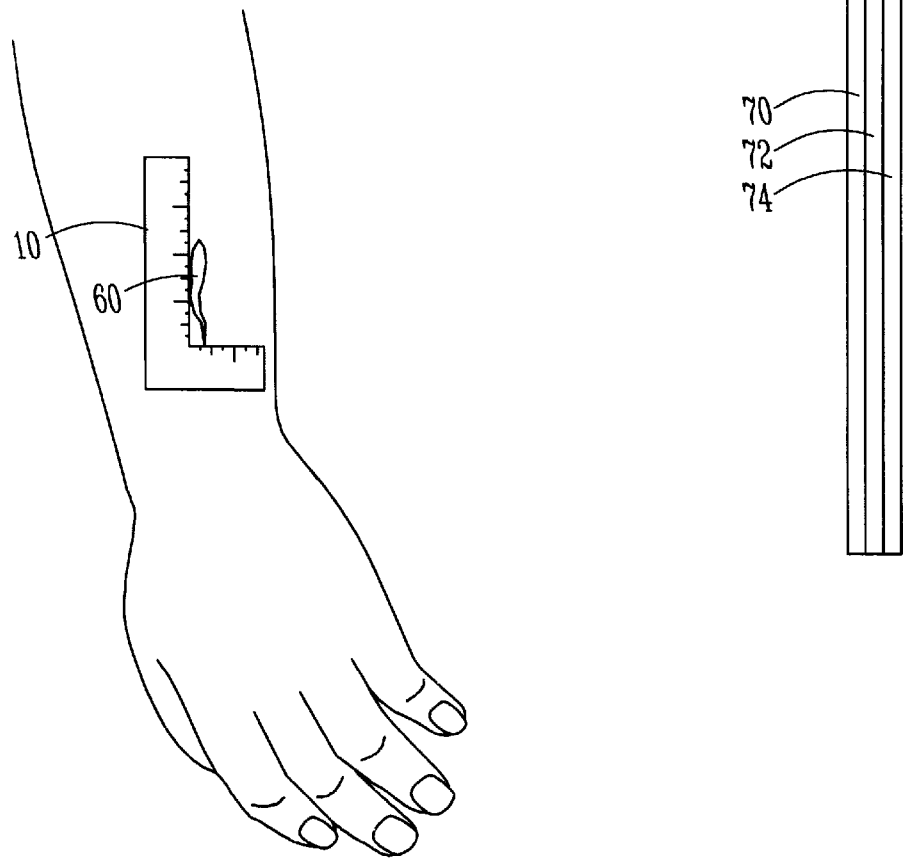
Fig. 5
Fig. 6

CUSTOMIZED AESTHETIC AND RECONSTRUCTIVE TEMPORARY TATTOO AND METHOD FOR MAKING SAME

BACKGROUND OF THE INVENTION

Many men, women and children undergo reconstructive surgery every year. This is oftentimes done to improve or restore their appearance by replacing a body part which has been lost or removed or to cover an undesirable scar or defect. Common forms of reconstructive surgery involve recreation of the breast mound after mastectomy, removal of surface abnormalities such as scars or vascular malformations, removal of tumors and reconstruction of the defect or restoration of normal anatomy following correction of a congenital defect.

For example, women (and occasionally men) must sometimes undergo mastectomy which removes all or portions of their breast with or without the nipple and areolar complex. Following this surgical procedure, many of these patients elect to undergo reconstructive surgery to recreate their breast mound either utilizing an implantable prosthetic device or with their own tissue. Although not restoring function, these procedures do improve their physical appearance and restore balance to the chest wall. Other patients who have been in accidents sustaining severe scarring or have lost body parts, individuals who have been in fires and sustained thermal injury or patients who have been born with congenital abnormalities may also require or elect to have reconstructive surgery to restore their normal appearance and function. Currently there are also nonsurgical options for reconstruction such as prosthetic breasts which are worn on top of the chest wall to restore forward projection in a bra. Rubbed on surface cosmetics have been used to cover scars. Professional tattooing is also currently being used to cover scars and other surface defects, as well as simulate body parts which are missing (eyebrows). Unfortunately, these nonsurgical options are not perfect and oftentimes have contraindications which prevent the patient from utilizing them.

Although there are a number of implantable prostheses and tissue types which simulate the shape and texture of a natural breast, none of them create a natural-appearing breast mound because they all lack a nipple and areolar complex. A patient, who for a number of reasons cannot have immediate reconstruction, has a significant chest wall defect not only because of a lack of breast mound, but because the nipple and areolar complex is absent, as well. The existing implantable breast prostheses and the tissue reconstruction options fall short in recreating the nipple and areolar complex and lack a normal nipple prominence shape and color. This makes the reconstruction inadequate and a third stage, i.e., nipple and areolar reconstruction, is considered the last phase of breast reconstruction. Oftentimes, however, patients for one reason or another are unable to undergo this final stage for months and continue to lack the shape and color of the nipple and areolar complex. The implantable prosthesis disclosed in U.S. Pat. No. 4,778,465 (Wilkins) tries to recreate the nipple prominence, but, unfortunately, the skin that overlies this implant is normal chest wall skin and scar only without color or texture of the normal nipple and areolar complex.

Three dimensional prosthetic nipple and areolar complexes, which are applied to the outside of the chest wall skin after reconstruction of the breast mound, do attempt to approximate a natural nipple shape, texture and color (U.S. Pat. No. 5,171,321—Davis). These prosthetic devices attach to the skin of the chest wall via adhesive or suction. However, since their inner surface is concave in order to attach and stay firmly adherent to the body, a close approximation to the breast mound or at least the chest skin must be present in order for it to work. Very often a good surface does not exist and these non-customized, limited-shaped, prosthetic nipples do not and will not fit on the mastectomized chest wall well. Patients become discouraged with their lack of fit and are always having to reapply them. Also, because these particular prosthetic nipple and areolar devices are not customized, the patient cannot adjust for individual size or shape and there is no clear method for matching these devices to the skin tone of the patient. Because there is constant motion of the breast mound and chest wall dislodgement of these prostheses occurs constantly even if attempted to be held on by adhesion or suction. Therefore, they always look unnatural and the patient is reluctant to wear them.

Another problem with the existing methods of nipple and areolar reconstruction (permanent tattooing, surgical creation of a nipple and areolar complex, glued on devices) is that often they cannot be utilized until a significant amount of time has passed after the initial breast mound reconstruction. This is due to the constraints of healing, chemotherapy, radiation and recovery time for the patient. The reconstructive processes oftentimes take many months. There must be enough time allowed for surgical incision healing, resolution of swelling, the expansion process, any revisions that might need to be provided and the patient's systemic illnesses possibly brought on by chemotherapy and radiation. All of these considerations require time and the patient while waiting for treatment in time to progress wants to look as natural as possible to allow them to get on with their lives. The current methods for aesthetic improvements do not enable these women to achieve this goal.

Devices for customizing the color of a prosthetic device have been disclosed, such as U.S. Pat. No. 4,735,754 (Buckner) and No. 5,727,567 (Karnaby, et al). These methods basically involve a labor-intensive process of painting the desired image onto the prosthetic device or layering latex in varying colors on the prosthetic device in order to produce a more realistic skin tone appearance. U.S. Pat. No. 5,798,062 (Thielbar) discloses a method of creating a breast/nipple prosthesis that is worn on the outside of the body and is color matched. However, these methods disclosed in the prior methods are deficient in that the colors must be applied to the prosthetic device itself and may not be applied directly to the skin thereby allowing the same displacement complaints. The prior methods are also deficient in that only stock colors are provided and the user must try herself to mix them in order to achieve the desired pigmentation to match her skin tones. Furthermore, matching is done visually, which is not as accurate as the formation of a computerized digital image followed up by an accurate printing method which produces a more exact reproduction of the skin tone size and shape.

Permanent tattooing in order to replace a missing body part or to cover a portion of the body is another option existing to improve or alter a patient's appearance. However, this method has many undesirable consequences. It is painful, there is a real risk of contracting HIV or hepatitis and a permanent tattoo cannot be altered to match the changing skin tones of an aging patient. Furthermore, the use of a permanent tattoo is undesirable in the case of a lost eyebrow because it cannot be removed when the natural eyebrow grows back. The present invention eliminates all of these concerns.

SUMMARY OF THE INVENTION

The present invention seeks to overcome the problems in these existing devices and methods by helping to improve the appearance of a woman's chest wall by simulating a nipple and areolar complex which realistically matches her own natural nipple and areolar skin tone, size and shape.

The present invention entails capturing the image of the body part to be removed, or of the corresponding opposite body part (such as second eyebrow or other areola complex) such as by taking a photograph and customizing a temporary applique or tattoo which can be applied directly to the skin. In addition, should a photo not be available, a catalog of similar body parts may be available to allow the patient/user or an other individual (such as a physician) to select a tattoo for use.

The invention claimed is the customized digital imaging of the temporary tattoo itself and also the method of creating the customized temporary tattoo. The method of transferring the tattoo from the substrate to the body, and the construction of the actual temporary tattoo card are not claimed. Methods of creating temporary tattoos such as those described in U.S. Pat. No. 4,169,169 (Katabatake), U.S. Pat. No. 4,594,276 (Relyea), and other well known methods for creating a temporary tattoo and for the means of its application to the body are acceptable methods for use with this invention and are incorporated by this reference. Tattoos should preferably be made with only FDA certified pigments and cosmetic ingredients. The temporary tattoo, which may be applied with water should last six to fourteen days, depending on skin type, including through swimming and showers. They can be removed with baby oil or rubbing alcohol. The present invention is a method to create a realistic temporary tattoo matched to the patient's individual skin tone, size and shape of their natural body part. It is also important that this method is able to custom design a temporary tattoo to match the actual body part of an individual patient.

This present invention can also be used immediately with no wait time. It is painless, lasts for several days, can be altered, if needed, and stays in place without displacement.

Besides its use in nipple and areolar reconstruction, the present invention can also be utilized for many other purposes. It can be applied to any area of the body where a body part has been removed or lost to create the lost part. For example, when an individual loses or has removed an eyebrow, their facial appearance can be restored by using a temporary customized replacement eyebrow to simulate the lost one while waiting for the natural eyebrow to either regrow or be reconstructed. It is preferable to match the replacement brow as closely as possible to the other intact eyebrow or to the one that was removed so that the improvement is as natural as possible. This present invention could also be used similarly to match features such as a mustache, a hairline or a sideburn area, which has been lost and needs to be replaced.

Another use of the present invention would be to cover or mask undesirable portions of the body such as scars, abnormally pigmented areas (such as lower eyelid darkening), moles and other large pigmented areas which may not have a surgical option, as well as stretch marks thereby improving the patient's appearance. These customized tattoos could also cover up telangiectasias, angiomas, spider veins, hemangiomas, arteriovenous malformations, hyperpigmentation, melasma, vitiligo, inflammatory areas, cysts, acne, keloids, freckles, lentigos, etc. The present invention could be used to cover a permanent tattoo which the patient no longer wishes to have exposed or may wish to cover on certain occasions. It could also be used to apply semi-permanent eyeliner or mascara. The existing art discloses methods of removing skin discolorations, which might include laser treatments and topical solutions, such as alpha hydroxy lotion or makeup cover-up. However, these methods of removal or cover-up can be painful, cause irritation, can scar the skin, might require multiple treatments, will not be totally effective, and might be expensive. The present invention eliminates these problems in that it is a quick, easy, painless method of covering the undesirable area.

BRIEF DESCRIPTION OF THE DRAWINGS

FIG. 4 is a perspective view of the catalog with clear pages that can be used to display a variety of tattoos in different sizes, shapes, and colors.

FIG. 5 is a view of a user having a scar photographed for coverage by a tattoo.

FIG. 6 is a side sectional view of the tattoo showing an adhesive layer, a digital image, and a backing material.

DESCRIPTION OF A PREFERRED EMBODIMENT OF THE INVENTION

Figure 1:
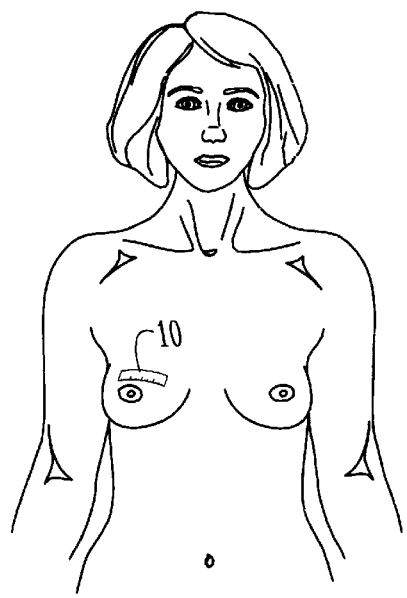
FIG. 1 is a drawing wherein the user of the present invention is having a photo taken before surgery to remove a body part or a catalog photo is being taken.

The present invention is a method of creating a photo-realistic temporary tattoo 30 that matches the skin tone, size and shape of a part of a person's body. The tattoo is generally of the type well known in the art, having a backing 70, an image 72, and an adhesive 74 which bonds the image 72 to the user.

The present invention may include the steps of: Taking photographs of various different body parts to create a stock sample or photographing a particular area on an individual patient to create a customized tattoo, developing the photographic film, scanning the photographs onto a computer to produce a digital image, producing an exact line drawing of the image, printing a corresponding line drawing on the reverse side of the temporary tattoo for alignment, and finally printing the digital image on the front side of the temporary tattoo.

One embodiment of the present invention involves taking the photographs of various body parts of many individuals in order to create a stock selection of tattoos representing various age groups, skin tones, sizes and shapes of each body part to be recreated. Another embodiment of the present invention includes taking photographs of the exact body part that is to be removed in advance (FIG. 1) so that the temporary tattoo is a more exact recreation of that particular individual's body part. A further embodiment of the present invention involves taking photographs of the other half of the paired body part (FIG. 1A) in order to create a customized temporary tattoo which replaces the lost part. Another embodiment to the tattoo results from a photo taken of an item to be covered, such as a scar 60. In this embodiment, agents can be added to the tattoo to aid in healing (for example, antiseptic, antibiotic) or to minimize scarring (for example, sun screen, vitamin E).

Figure 1A:
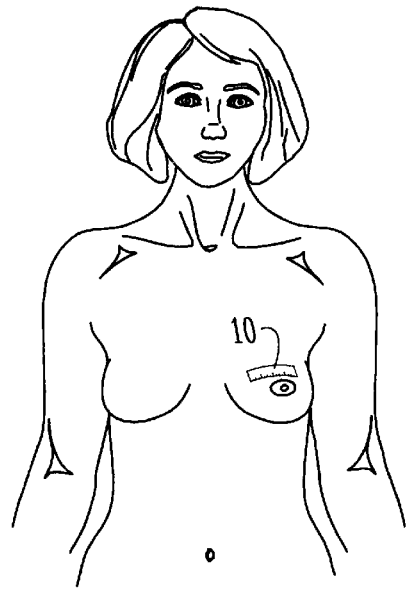
FIG. 1A is a drawing showing a user having the photograph of a corresponding body part being taken so that a matching tattoo can be made for the missing body part.
Figure 2:
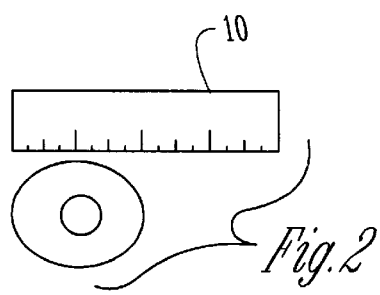
FIG. 2 is a close-up view of an adhesive ruler place above the areola complex.
Figure 3:
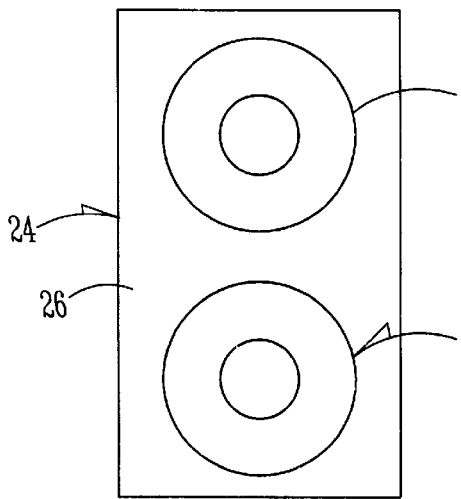
FIG. 3 is a view of the tattoo card showing the line drawing used for alignment and placement of the tattoo.

When taking photos of an individual customer to produce a customized tattoo, disposable transparent malleable adhesive rulers 10 may be placed in the area to be photographed to ensure that the tattoo is customized to the exact size and shape desired. The rule 10 may be linear (as shown in FIG. 1) or provide measurement in more than one dimension (see FIG. 5) for more accurate sizing. After the photographs are taken, the film is developed by a production artist. The prints are scanned onto a computer to produce a digital image. The preferred embodiment uses a flatbed scanner and a software program such as "Adobe Photo Shop." The production artist then retouches and corrects any color defect in the digital image. A corresponding line drawing 20 of the digital image may be rendered. This line drawing 20 is printed to match the temporary tattoo on the opposite side and is used for alignment during the application of the tattoo. It may be an exact duplication of the actual tattoo on the other side, or a simple lined schematic for alignment as shown in FIG. 3. This preferred embodiment uses a software program such as "Macromedia Freehand," to create the line drawing.

This image of the tattoo 30 is then placed, using a layout program, on the front 22 of a temporary tattoo card 24 on which the line drawing may have already been placed on the reverse side 26. Another alignment line 40 may be positioned around the image 30 to show the boundary of the tattoo 30. This line is optional. Although on the same side 22 of card 24, the line 40 will not print when the tattoo 30 is applied. Multiple tattoos 30 may be placed on a card 24 to accommodate for multiple applications.

The preferred embodiment utilizes a software program, such as "Quark Xpress," for this step. These digital files are then collected for print onto a disk. The disk, print work order form, output specification sheet and a laser proof are sent to the printer. A match proof of each temporary tattoo is then generated by the printing company and closely reviewed and compared to the photographs in order to ensure that the temporary tattoo is a realistic photo match. At that time, the patient may also want to view the proof of the temporary tattoo if it is a custom made item. The temporary tattoos are then printed and shipped to the production artist. The product is then packaged and shipped to the individual customer in the example of a custom-made tattoo or used in the stock supply and stored for future orders. The temporary tattoo is then ready for placement on the patient. The digital file is saved, preferably burned onto a CD and archived for future use.

Figure 3A:
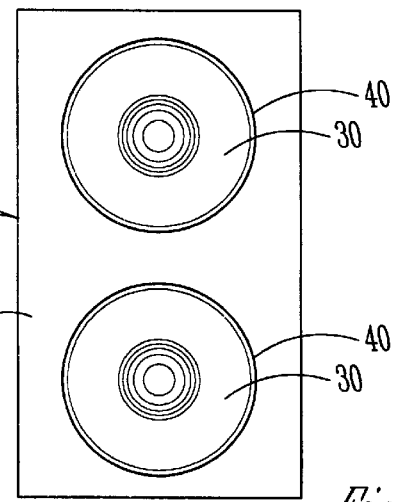
FIG. 3A is a view of the tattoo card showing the tattoo that is to be placed on a user/patient. Although represented in simple line fashion, the tattoo would be visually similar if not identical to the body part being replicated.

To facilitate ordering from the stock supplies of temporary tattoos (those that are not created for a specific individual), the present invention utilizes a swatch book and a catalog 50. Each age grouping, skin tone grouping and size grouping of every temporary tattoo 30 is digitally output on a transparent film overlay 54. The overlay shown in FIG. 4 provides two specimens 30 per page 54, although in practice, one specimen per page is often times preferred as this allows the patient to hold one tattoo 30 up to his/her skin and view how it will look when applied. These overlays may be held together by a rivet 52 to create a swatch book of temporary tattoo body parts. The rivet 52 may be removable to allow easy use and placement of the specimen on the user. The swatch book is used by the physician and patient to select either a body part that closely represents the original body part or a body part that most closely matches the patient's own skin tone, shape and size. An alignment line is believed to be unnecessary, but may be used if desired (as shown in FIG. 3A on card 24).

The transparent quality of the swatch book allows the patient to hold the image next to their body or over their skin to assist in matching and selecting the appropriate tattoo in order that a natural appearance might be achieved for the finished product. A catalog might also be used in the ordering process which shows printed samples of all the various temporary tattoo body parts. This method would be less expensive to produce than the swatch book and might be removed from the physician's office and taken to the privacy of the patient's home.

An example of the preferred embodiment is the nipple and areolar complex. However, this method can be used to create temporary tattoos for a host of other surface defects, such as: the eyebrow (mustaches, hairlines and sideburns), concealment of nevi and other pigmented tumors (keratoses), scars, lower eyelid pigmentation (undereye shadow), telangiectasias, angiomas, spider veins, created or traumatic tattoos, hemangiomas, arteriovenous malformation, striae (stretch marks), hyperpigmentation, melasma (dark spots following pregnancy), vitiligo (white spots or deep pigmentation areas), inflammation, cysts, acne, keloids, hypertrophic scars, freckles, lentigos. These temporary tattoos can also be used for cosmetic enhancements, such as eyelid liner and mascara. Custom anatomic tattoos can also be used to allow a person to temporarily assume the appearance of another or of a fictional character (such as the character Darth Maul™).

Although particular embodiments of the invention have been described in detail, it will be understood that the invention is not limited to the embodiments discussed above, and there may be other embodiments which fall within the spirit and scope of the invention as defined by the following claims. For example, the tattoo 30 may be hand drawn as opposed to a digital image. The above description is considered illustrative, and not restrictive in character.

What is claimed is:

1. A method of making a cosmetic temporary tattoo comprising the steps of:
    placing a disposable malleable adhesive ruler in an area to be photographed;
    capturing the image of an individual body part in order to produce a custom-matched temporary tattoo according to the size, shape and color of a specific body part;
    creating a temporary tattoo to replicate the size, shape and color of the captured image; and
    applying the tattoo to an individual.

2. A method of claim 1 wherein the image is captured by making a photograph and scanning the photograph to produce a digital image.

3. The method of claim 2 further comprising the step of printing a line drawing on the reverse side of the temporary tattoo to aid in alignment.

4. A method of making a catalog of cosmetic temporary tattoos comprising the steps of:
    placing a disposable malleable adhesive ruler in an area to be photographed;
    capturing images of individuals having body parts of various sizes, shapes and colors;
    producing a temporary tattoo of each of the captured images of body parts; and
    placing the temporary tattoo form into a catalog for review by a user.

5. The method of claim 4 wherein the catalog is comprised of clear pages for display of the temporary tattoos.

6. The method of claim 5 further comprising the steps of:

selecting a temporary tattoo from the catalog; and applying the temporary tattoo to the user.

7. The method of claim 6 further comprising the step of:

retouching said image in the catalog; and color correcting said digital image to correspond with the individual body part attempting to be matched.

8. A temporary tattoo comprising:

a backing material having a front side and a back side;

a tattoo image located adjacent the front side of the backing material;

an adhesive layer located adjacent the tattoo image; and a line drawing of the tattoo image on the back side of the backing material to aid an alignment of the temporary tattoo.

* * * * *